United States Patent
Laugraud et al.

Patent Number: 5,985,853
Date of Patent: Nov. 16, 1999

[54] β-METHOXY ACRYLIC ACID DERIVATIVES, METHOD FOR PREPARING SAME, AND USE OF SAID DERIVATIVES AS PESTICIDES

[75] Inventors: Sylvain Laugraud, deceased, late of Paris; by Pierre Laugtaud, legal representative, Paris; by Rolande Laugraud, legal representative, Mantes-la-Ville; by Philippe Laugraud, legal representative, Jouy le Motier; by Bruno Laugraud, legal representative, Mantes la Ville; by Martine Sollossi, legal representative, Jouy le Moutier; Nicole Reinier, Marseille, all of France

[73] Assignee: Hoechst Marion Roussel, France

[21] Appl. No.: 08/945,013

[22] PCT Filed: Apr. 11, 1996

[86] PCT No.: PCT/FR96/00544

§ 371 Date: Dec. 4, 1997

§ 102(e) Date: Dec. 4, 1997

[87] PCT Pub. No.: WO96/32399

PCT Pub. Date: Oct. 17, 1996

[30] Foreign Application Priority Data

Apr. 14, 1995 [FR] France .................................. 95 04506

[51] Int. Cl.⁶ .................................................. A01N 55/10
[52] U.S. Cl. ........................... 514/63; 556/437; 556/438; 556/441; 556/426; 556/465; 556/449; 556/415; 556/417; 556/446
[58] Field of Search ............................... 514/63; 556/437, 556/438, 441, 465, 449, 413, 415, 417, 426, 445, 446

[56] References Cited

FOREIGN PATENT DOCUMENTS 0601477  6/1994  European Pat. Off. .

*Primary Examiner*—Gary Geist
*Assistant Examiner*—Jean F Vollano
*Attorney, Agent, or Firm*—Bierman, Muserlian and Lucas

[57] ABSTRACT

A subject of the invention is the products of formula (I):

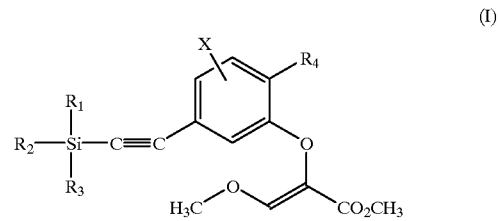

in which:

$R_1$, $R_2$ and $R_3$, identical or different, represent a linear, branched or cyclic alkyl radical, an alkenyl or alkynyl radical, containing up to 8 carbon atoms, optionally substituted by one or more halogen atoms, an aryl radical optionally substituted by one or more halogen atoms, one or more hydroxyl radicals, one or more linear or branched alkyl radicals, optionally substituted by one or more halogen atoms, one or more O-alkyl or S-alkyl radicals optionally substituted by one or more halogen atoms, X represents a hydrogen atom, a halogen atom, an alkyl, alkenyl, alkynyl, O-alkyl, O-alkenyl, O-alkynyl, S-alkyl, S-alkenyl or S-alkynyl radical, optionally substituted by one or more halogen atoms and containing up to 11 carbon atoms, an aryl radical containing up to 14 carbon atoms, a C≡N, $NO_2$, $NH_2$,

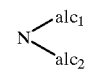

$CO_2$ $alk_3$ radical, $alk_1$, $alk_2$ and $alk_3$, identical to or different from each other, representing an alkyl radical containing up to 8 carbon atoms, $R_4$ represents one of the values indicated above for X with the exception of hydrogen.

11 Claims, No Drawings

β-METHOXY ACRYLIC ACID DERIVATIVES, METHOD FOR PREPARING SAME, AND USE OF SAID DERIVATIVES AS PESTICIDES

This application is the national phase of PCT/FR96/00544 filed Apr. 11, 1996.

The present invention relates to new derivatives of β-methoxy acrylic acid, their preparation process and their use as pesticides.

A subject of the invention is the compounds of formula (I):

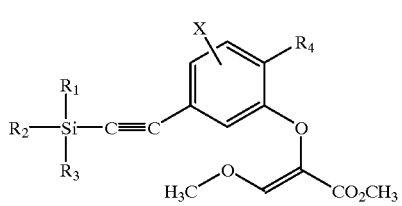

in which:
- $R_1$, $R_2$ and $R_3$, identical or different, represent a linear, branched or cyclic alkyl radical, an alkenyl or alkynyl radical, containing up to 8 carbon atoms, optionally substituted by one or more halogen atoms, an aryl radical optionally substituted by one or more halogen atoms, one or more hydroxyl radicals, one or more linear or branched alkyl radicals, optionally substituted by one or more halogen atoms, one or more O-alkyl or S-alkyl radicals optionally substituted by one or more halogen atoms,
- X represents a hydrogen atom, a halogen atom, an alkyl, alkenyl, alkynyl, O-alkyl, O-alkenyl, O-alkynyl, S-alkyl, S-alkenyl or S-alkynyl radical, optionally substituted by one or more halogen atoms and containing up to 11 carbon atoms, an aryl radical containing up to 14 carbon atoms, a C≡N, $NO_2$, $NH_2$,

$CO_2$ $alk_3$ radical, $alk_1$, $alk_2$ and $alk_3$, identical to or different from each other, representing an alkyl radical containing up to 8 carbon atoms,
- $R_4$ represents one of the values indicated above for X with the exception of hydrogen.

The geometry of the double bond of the β-methoxy acrylic part can be Z, E or an E+Z mixture.

In the definition of the various substituents:
- alkyl preferably represents a methyl, ethyl, propyl, isopropyl, butyl, isobutyl, sec-butyl, terbutyl radical, linear or branched pentyl, hexyl, heptyl or octyl,
- the cyclic alkyl radical preferably represents a cyclopropyl, cyclobutyl or cyclopentyl radical,
- the alkenyl or alkynyl radical is preferably an ethenyl, ethynyl, propenyl, propynyl, butenyl or butynyl radical,
- the heterocyclic radical is preferably a pyrrolidinyl, pyrazolinyl, piperidinyl, piperazinyl or morpholinyl radical,
- the aryl radical is preferably a phenyl radical.

A more particular subject of the invention is the compounds of formula (I) in which the geometry of the exo double bond (enol ether) is Z.

A particular subject of the invention is the compounds of formula (I) in which $R_1$, $R_2$ and $R_3$ each represent an alkyl radical containing up to 4 carbon atoms and in particular those in which $R_1$, $R_2$ and $R_3$ each represent a methyl or ethyl radical, as well as those in which $R_4$ represents a halogen atom, as well as those in which $R_4$ represents an alkyl radical containing up to 4 carbon atoms.

Among the preferred compounds of the invention, there can be mentioned more particularly those whose preparation is given hereafter in the experimental part and quite especially the compounds of Examples 1, 4 and 5.

Also a subject of the invention is a preparation process for the compounds of formula (I) characterized in that a compound of formula (II):

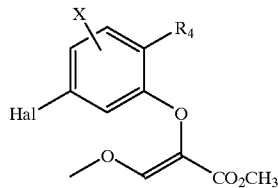

in which Hal represents a halogen atom, X and $R_4$ retain their previous meaning, is subjected to the action of a compound of formula (III):

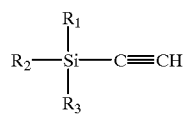

in which $R_1$, $R_2$ and $R_3$ retain their previous meaning, in order to obtain the corresponding compound of formula (I).

In a preferred implementation of the process of the invention, the reaction between the compound of formula (II) and the compound of formula (III) is carried out in an aprotic dipolar solvent such as acetonitrile or dimethyl formamide, in the presence of a tertiary amine such as triethylamine, and in the presence of palladium, for example in the presence of bis(triphenylphosphine) palladium (II) chloride, or metallic palladium on a charcoal support, of a tertiary phosphine such as triphenylphosphine and a copper-based catalyst such as cuprous iodide, Hal preferably represents a bromine or iodine atom.

The compounds of formula (II) are new products and are in themselves a subject of the present invention.

The compounds of formula (II) can be prepared according to the reaction diagram:

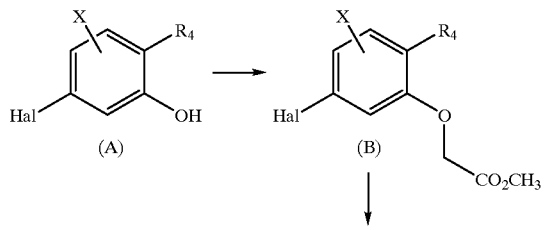

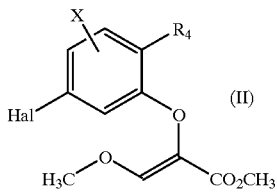

The starting product of formula (A) can be prepared according to the following process:

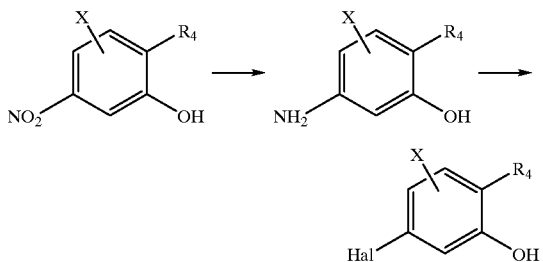

The compounds of formula (II) can also be prepared according to the following reaction diagram:

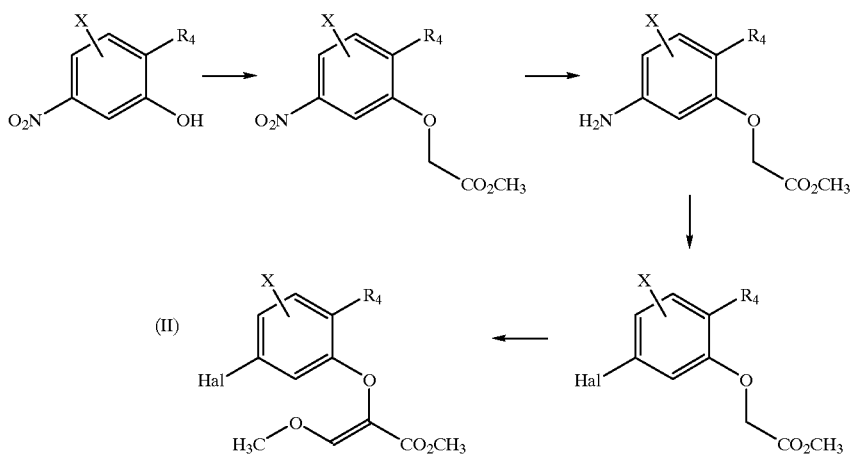

The experimental part set out hereafter gives examples of the preparation of the compounds of formula (II).

The compounds of formula (I) have useful properties which allow their use for combating parasites. It can be for combating parasites of vegetation whether they be parasites of the soil or of the parts above ground, parasites of premises and parasites of animals.

The compounds of formula (I) have insecticide, acaricide and nematicide properties as well as fungicide properties.

The products of formula (I) can thus be used for combating insects in premises, for combating in particular flies, mosquitoes and cockroaches.

The products of formula (I) can also be used to combat insects and other parasites of the soil, for example Coleoptera, such as Diabrotica, click beetles and May beetle grubs, Myriapoda such as Scutigeridae and blanjules, and Diptera such as Cecydomia and Lepidoptera such as owlet moths.

The products of formula (I) also possess excellent acaricide activities as is shown by the results of the biological tests which appear hereafter.

The products of formula (I) can also be used to combat parasitic acaridae of vegetation.

The compounds of formula (I) can also be used to combat parasitic nematodes of vegetation.

The compounds of formula (I) can also be used to combat parasitic acaridae of animals, to combat for example ticks and notably ticks of the Boophilus species, those of the Hyalomnia species, those of the Amblyomnia species and those of the Rhipicephalus species, or to combat all types of mites and in particular the sarcoptic mite, the psoroptic mite and the chorioptic mite.

Therefore a subject of the invention is also the compositions intended for combating parasites of warm-blooded animals, parasites of premises and of vegetation, characterized in that they contain at least one of the products defined above.

The compositions according to the invention are prepared according to the usual processes of the agro-chemical industry or the veterinary industry or the industry for products intended for animal nutrition.

In these compositions intended for agricultural use and for use in premises, the active ingredient or ingredients can optionally have one or more other pesticide agents added to it/them. These compositions can be presented in the form of powders, granules, suspensions, emulsions, solutions, solutions for aerosols, combustible strips, baits or other preparations usually employed for the use of this type of compound.

In addition to the active ingredient, these compositions contain, in general, a non-ionic vehicle and/or a surfactant, providing, moreover, a uniform dispersion of the constitutive substances of the mixture. The vehicle used can be a liquid, such as water, alcohol, hydrocarbons or other organic solvents, a mineral, animal or vegetable oil, a powder such as talc, clays, silicates, kieselguhr or a combustible solid.

A particular subject of the invention is the insecticide compositions containing as active ingredient at least one of the products defined above.

The insecticide compositions according to the invention preferably contain 0.005% to 10% by weight of active ingredient.

According to an advantageous operating method, for a use in premises, the compositions according to the invention are used in the form of fumigant compositions.

The compositions according to the invention can then be advantageously constituted, for the non-active part, by a combustible insecticide coil or also an incombustible fibrous substrate. In this last case, the fumigant obtained after incorporation of the active ingredient is placed on a heating apparatus such as an electric vaporizer.

In the case where an insecticide coil is used, the inert support can be, for example, pyrethrum marc compound, Tabu powder (or Machilus Thumbergii leaf powder), pyrethrum stem powder, cedar leaf powder, sawdust (such as pine sawdust), starch and coconut shell powder.

The dose of active ingredient can then be, for example, 0.03 to 1% by weight.

In the case where an incombustible fibrous support is used, the dose of active ingredient can then be, for example, 0.03 to 95% by weight.

The compositions according to the invention for a use in premises can also be obtained by preparing a sprayable oil based on the active ingredient, this oil impregnating the wick of a lamp and then being set alight.

The concentration of active ingredient incorporated in the oil is, preferably, 0.03 to 95% by weight.

The insecticide compositions according to the invention, such as the acaricide and nematicide compositions, can optionally have added to them one or more other pesticide agents. The acaricide and nematicide compositions can be presented in the form of powders, granules, suspensions, emulsions, solutions.

In addition, a subject of the invention is the acaricide compositions containing as active ingredient at least one of the products of formula (I) as defined previously.

For acaricide use, there are preferably used wettable powders, for foliar spraying, containing 1 to 80% by weight of active ingredient, or liquids for foliar spraying containing 1 to 500 g/l of active ingredient. Powders for foliar dustings can also be used containing 0.05 to 3% of active ingredient.

For nematicide use, liquids are preferably used for soil treatment containing 300 to 500 g/l of active ingredient.

The compounds of formula (I) have an excellent fungicide activity. They allow the combating of fungi which have already penetrated inside the tissues of vegetation. This is particularly useful in the case where it is no longer possible to combat diseases caused by fungi once the contamination has already taken place. The spectrum of activity of the compounds of formula (I) covers a great number of phytopathogenic fungi of varied economic importance, for example *Pyricularia oryzae, Venturia inaequalis, Cercospora beticola,* Erysiphicaceae (Sp. powdery mildew), Fusarium-, Drechslera- and Leptosphaeria-, *Plasmopara viticola, Phytophtora infestans, Pseudoperonospora cubensis,* various rusts, strains of *Botrylis cinerea* susceptible and resistant to BCM- and/or to Dicarboximide-, *Sclerotinia solerotiorum,* strains of *Pseudocercosporella herpotrichoides*-resistant to BMC and *Pellicularia sasakii.*

Therefore a quite particular subject of the invention is the fungicide compositions containing as active ingredient at least one of the products of formula (I) as defined previously and more especially the fungicide compositions containing 0.001 to 1% by weight of compounds of formula (I).

Moreover, the compounds of the invention can also be used in different industrial sectors for example to protect wood or as a preserving agent for paints.

The invention also extends to the fungicide compositions which contain, in addition to the compounds of formula (I), suitable formulation agents.

The compositions of the invention contain in general 1 to 95% by weight of active ingredient.

The possible formulations vary as a function of the biological and physico-chemical parameters. They can be for example wettable powders, emulsifiable concentrates, aqueous solutions, emulsions, solutions for vaporization, dispersions in oil or in water, suspoemulsions, powders, agents for the treatment of seeds, granules, for example microgranules, granules for pulverization, coated granules, absorption granules, granules dispersible in water, ULV formulation, microcapsules, waxes or baits.

The following examples illustrate the invention without however limiting it.

EXAMPLE 1

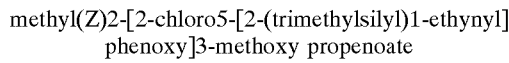
methyl(Z)2-[2-chloro5-[2-(trimethylsilyl)1-ethynyl]
phenoxy]3-methoxy propenoate A mixture containing 0.9 g of the product of Preparation 1, 0.78 ml of trimethylsilyl acetylene, 78 mg of $PdCl_2$ $(PPH_3)_2$ and 21 mg of copper iodide, 10 ml of acetonitrile and 5 ml of triethylamine is taken to reflux under a nitrogen atmosphere for 3 hours. Reflux is maintained for 2 hours. The solution is evaporated under reduced pressure, the residue is taken up in methylene chloride and washed with water. The organic phase is dried over magnesium sulphate and evaporated under reduced pressure. The product obtained is chromatographed, eluting with a hexane-ethyl acetate mixture (8/2). In this way 0.88 g of sought product is obtained, melting at 148° C.

NMR $CDCl_3$ ppm 0.24 (s): $Si(CH_3)_3$; 3.73 (s)–3.89 (s): $OCH_3$; 6.88 (d): $H_3$; 7.05 (dd): $H_5$; 7.29 (d): $H_6$; 7.36 (s): ΔZ ethylenic hydrogen.

EXAMPLE 2

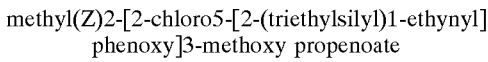
methyl(Z)2-[2-chloro5-[2-(triethylsilyl)1-ethynyl]
phenoxy]3-methoxy propenoate By operating as previously with triethylsilyl acetylene, the sought product is obtained. M.p.=93° C.

NMR $CDCl_3$ ppm 0.66 (q)–1.03 (t): the protons of the ethyls; 3.73 (s)–3.89 (s): the protons of the methoxys; 6.87 (d): $H_6$; 7.06 (dd): $H_4$; 7.30 (d): $H_3$; 7.37 (s): HΔZ.

Preparation of the starting product of Example 1
and of Example 2

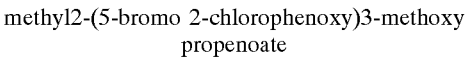
methyl2-(5-bromo 2-chlorophenoxy)3-methoxy
propenoate

Stage A: 5-bromo 2-chlorophenol 9 ml of boron tribromide is added dropwise to a solution containing 20 g of 5-bromo 2-chloro anisole in 200 ml of methylene chloride. Agitation is carried out for 10 minutes at 0° C., then for 24 hours at 20° C. and the reaction medium is poured into a water and ice mixture. The resultant suspension is agitated for 30 minutes, extraction is carried out with methylene chloride, followed by saturation with sodium chloride and extraction twice with methylene chloride. The organic phases are collected, dried over magnesium sulphate, evaporated under reduced pressure and 18.5 g of 5-chloro 2-bromophenol is obtained. M.p.=56° C.

Stage B: methyl (5-bromo 2-chlorophenoxy) acetate 12 g of potassium carbonate is added to a solution containing 9 g of the product prepared in Stage A and 4.3 ml of methyl bromoacetate in 200 ml of anhydrous acetone. The suspension obtained is heated under reflux, under a nitrogen atmosphere for 3 hours, poured into water and extraction is carried out with methylene chloride. The organic phases are collected, washed with a saturated solution of sodium chloride, dried over magnesium sulphate and evaporated under reduced pressure. After washing with pentane, 11.4 g of sought product is obtained, melting at 72° C.

Stage C: methyl (ΔZ) 2-(5-bromo 2-chlorophenoxy) 3-methoxy propenoate

A suspension of 9 g of the product obtained in Stage B in 75 ml of bis-dimethylamino terbutoxy methane is heated at 80° C. for one hour. The temperature is left to return to 20° C., the reaction medium is poured into water and extraction is carried out with methylene chloride. The organic phases are collected, dried over magnesium sulphate and evaporated under reduced pressure.

The preceding residual oil is taken up in 300 ml of THF. 100 ml of 2N hydrochloric acid is added slowly to this solution, cooled down to 0° C. The reaction medium is agitated for one hour at 20° C., then it is poured into an aqueous solution saturated with sodium chloride, extraction is carried out with ethyl ether. The organic phases are collected, dried over magnesium sulphate, evaporated under reduced pressure.

The product thus obtained is taken up in 250 ml of acetone. 3.4 ml of methyl sulphate and 8.9 g of potassium carbonate are added. The suspension is agitated under a nitrogen atmosphere for 20 hours, poured into water and extraction is carried out with methylene chloride. The organic phases are collected, dried over magnesium sulphate and evaporated under reduced pressure. The product obtained is chromatographed on silica, eluting with a heptane-ethyl acetate mixture (75-25) and 9.95 g of sought product is obtained.

EXAMPLE 3 methyl(Z)2-[2-methoxy5-[2-(triethylsilyl)1-ethynyl]phenoxy]3-methoxy propenoate

By operating as in Example 1, starting with the starting product described hereafter and triethylsilyl acetylene in dimethylformamide and at 20° C., the sought product is obtained, melting at 104° C.

NMR $CDCl_3$ ppm 0.65 (q)–1.03 (t): the protons of the ethyls; 3.72 (s)–3.86 (s)–3.91 (s): OME; 6.82 (d): $H_6$; 6.84 (d): $H_5$; 7.12 (dd): $H_5$; 7.34 (s): HΔZ.

Starting product of Example 3 methyl(Z)2-(5-iodo2-methoxy phenoxy)3-methoxy propenoate

The starting product of Example 3 was prepared as follows:

Stage A: methyl (2-methoxy 5-nitro phenoxy) acetate 24.5 g of potassium carbonate is added to a solution containing 15 g of 2-methoxy 5-nitro phenol and 8.8 ml of methyl bromoacetate. The resultant suspension is heated under reflux and under a nitrogen atmosphere for 2 hours then it is poured into water and extraction is carried out with ethyl acetate. The organic phases are collected, washed with an aqueous solution saturated with sodium chloride, dried over magnesium sulphate and evaporated under reduced pressure. The residual solid is washed with pentane and 20.7 g of sought product is obtained, melting at 109° C.

Stage B: methyl (5-amino 2-methoxy phenoxy) acetate 0.66 g of 10% by weight of palladium on charcoal is added to a solution containing 3 g of the product prepared in Stage A, and 100 ml of ethyl acetate. The suspension obtained is agitated under 1.3 atmospheres of hydrogen. After the absorption of hydrogen has stopped, the pressure is returned to normal atmospheric pressure, followed by filtration and evaporation under reduced pressure. 2.6 g of sought product is obtained, melting at 79° C.

Stage C: methyl (5-iodo 2-methoxy phenoxy) acetate 2.02 g of product prepared in Stage B is added to a solution containing 20 ml of water, 6 ml of acetic acid and 1 ml of concentrated sulphuric acid. The suspension obtained is cooled down to 0° C. Then over 35 minutes a solution of 0.66 g of sodium nitrite in 5 ml of water is added dropwise. The solution obtained is agitated for 45 minutes at 0° C. A solution of 3.2 g of potassium iodide in 5 ml of water is then added dropwise over 40 minutes. The reaction medium is maintained under agitation for one hour at 0° C. then for 2 hours at 10° C., then for 16 hours at 20° C. It is poured into water and extraction is carried out with methylene chloride. The organic phases are collected, washed with water, with a saturated solution of sodium bicarbonate, with an aqueous solution of sodium bisulphite, dried over magnesium sulphate and evaporated under reduced pressure. The product obtained is chromatographed, eluting with methylene chloride. 2.0 g of sought product is obtained, melting at 100° C.

Stage D: methyl (Z) 2-(5-iodo 2-methoxy phenoxy) 3-methoxy propenoate

By operating as in the last stage of the preparation of the starting product of Examples 1 and 2, the sought product was obtained, melting at 116° C.

EXAMPLE 4 methyl(Z)3-methoxy2-[2-methyl5-[2-(trimethylsilyl)1-ethynyl]phenoxy]propenoate

By operating as in Example 1 but in the DMF and at 20° C., starting with appropriate starting products, the sought product was obtained, melting at 125° C.

NMR $CDCl_3$ ppm 0.24 (s): $Si(CH_3)_3$; 2.33 (s): the protons of $CH_3$ in position 2; 3.71 (s)–3.88 (s): the protons of the methoxys; 6.80 (d): $H_6$; 7.05 (m): $H_3$ and $H_4$; 7.32 (s): ΔZ ethylenic H.

EXAMPLE 5 methyl(Z)3-methoxy2-[2-methyl5-[2-(triethylsilyl)1-ethynyl]phenoxy]propenoate

By operating as in Example 1 but in DMF and at 20° C., starting with corresponding starting products, the sought product was obtained, melting at 93° C.

NMR $CDCl_3$ ppm 0.68 (q)–1.03 (t): the protons of the ethyl; 2.94 (s): the methyl in position 2; 3.71 (s)–3.80 (s): the methoxys; 6.79 (s)–7.06 (m): $H_3$, $H_4$ and $H_6$; 7.33 (s): ΔZ H.

EXAMPLE 6 methyl(Z)3-methoxy2-[2-methyl5-[2-(terbutyl dimethylsilyl)1-ethynyl]phenoxy]propenoate By operating as in Example 1 but in DMF and at 20° C., starting with corresponding starting products, the sought product was obtained, melting at 110° C.

NMR $CDCl_3$ ppm 0.10 (s) $Si(CH_3)_2$; 0.91 (s) SitBu; 2.27 (s) $CH_3$; 3.64 (s) and 3.81 (s) the OMe's; 6.71 (d) $H_6$; 6.95 (dd) $H_4$; 7.01 (d) $H_3$; 7.26 (s) ΔZ H.

EXAMPLE 7 methyl(Z)3-methoxy2-[2-methyl5-[2-(dimethyl phenyl silyl)1-ethynyl]phenoxy]propenoate By operating as in Example 1 but in DMF and at 20° C., starting with corresponding starting products, the sought product was obtained, melting at 94° C.

NMR CDCl$_3$ ppm 0.51 (s) Si(CH$_3$)$_2$; 2.37 (s) CH$_3$ in position 2; 3.73 (s) and 3.87 (s) the OMe's; 6.86 (s) H$_6$; 7.11 (s) H$_3$ and H$_4$; 7.35 (s) ΔZ H; 7.40–7.43 (m) 3H Silh; 7.69–7.73 (m) 2H Silh. Starting product of Examples 4 to 7: methyl(Z)2-(5-iodo 2-methylphenoxy) 3-methoxy propenoate Stage A: 5-iodo 2-methyl phenol 10 g of 5-amino 2-methyl phenol is dissolved in a solution of 150 ml of water, 100 ml of THF and 6 ml of concentrated sulphuric acid. The resultant solution is cooled down to 0° C. A solution of 5.6 g of sodium nitrite in 30 ml of water is added dropwise at 0° C. over 40 minutes. Next the suspension obtained is agitated for 30 minutes at 0° C. and 17.5 g of potassium iodide in 70 ml of water and 200 mg of powdered metallic copper are added. The temperature is left to rise to 20° C. over 30 minutes and agitation is maintained for one hour at this temperature. The reaction medium is poured into water and extraction is carried out with ethyl acetate. The organic phases are collected, dried over magnesium sulphate and evaporated under reduced pressure. The residual oil is chromatographed, eluting with a heptane-ethyl acetate mixture (1-1), in order to give 9.7 g of 5-iodo 2-methyl phenol. M.p.=60° C.

Stage B: methyl (5-iodo 2-methoxy phenoxy) acetate 9.45 g of potassium carbonate is added to a solution containing 8.02 g of 5-iodo 2-methyl phenol and 3.3 ml of methyl bromoacetate in 100 ml of anhydrous acetone. The reaction medium is heated under reflux and under a nitrogen atmosphere for 2 hours 30 minutes then poured into water and extraction is carried out 3 times with methylene chloride. The organic phases are collected, washed with an aqueous solution saturated with sodium chloride, dried over magnesium sulphate, then evaporated under reduced pressure in order to give 9.95 g of sought product.

Stage C: methyl (Z)2-(5-iodo 2-methyl phenoxy) 3-methoxy propenoate

A suspension of 8.2 g of the product prepared in Stage B in 40 ml of bis-dimethylamino terbutoxy methane is heated at 80° C. for one hour 30 minutes. After the temperature has returned to 20° C., the solution obtained is poured into water and extraction is carried out with methylene chloride. The organic phases are collected, dried over magnesium sulphate and evaporated under reduced pressure. The residual oil is taken up in 200 ml of THF. 100 ml of 2 hydrochloric acid is added slowly at 0° C. Agitation is carried out for 2 hours at 20° C., the reaction medium is poured into a saturated aqueous solution of sodium chloride and extraction is carried out with ethyl ether. The organic phases are collected, dried and evaporated under reduced pressure. The product obtained is taken up in 100 ml of acetone. 2.8 ml of methyl sulphate and 7.4 g of potassium carbonate are added. The suspension obtained is agitated under a nitrogen atmosphere for 3 hours, poured into water and extraction is carried out with methylene chloride. The organic phases are collected, dried over magnesium sulphate and evaporated under reduced pressure. The product obtained is recrystallized from 40 ml of isopropanol and 8.0 g of sought product is obtained, melting at 112° C.

EXAMPLE 8 methyl(Z)3-methoxy2-[4-[2-trimethylsilyl)1-ethynyl](1,1'-biphenyl)2-yloxy]propenoate By operating as in Example 1, but in DMF and at 20° C., starting with the starting product described hereafter, the sought product was obtained, melting at 131° C.

NMR CDCl$_3$ ppm 0.26: Si(CH$_3$)$_3$; 3.72 (s)–3.84: the OMe's; 6.94 (d): H$_6$; 7.18 (d): H$_4$; 7.28 (d): H$_3$; 7.33: ΔZ H; 7.31 (t) 1H: of the phenyl in position 2; 7.40 (t) 2H: of the phenyl in position 2; 7.67 (d) 2H: of the phenyl in position 2.

EXAMPLE 9 methyl(Z)3-methoxy2-[4-[2-triethylsilyl)1-ethynyl] (1,1'-biphenyl)2-yloxy]propenoate By operating as in Example 1, but in DMF and at 20° C., starting with the starting product described hereafter, the sought product was obtained, melting at 139° C.

NMR CDCl$_3$ ppm 0.70 (q) 6H: the protons of SiCH$_2$; 1.06 (t) 9H: CH$_3$; 3.73 (s) 3H; 3.84 (s) 3H; 6.94 (d) 1H; 7.15–7.45 (m) 6H; 7.67 (d) 2H.

Starting product of Examples 8 and 9

The starting product of Examples 6 and 7 was prepared as follows: methyl(Z)2-[4-iodo (1,1'-biphenyl)2-yloxy]3-methoxy propenoate Stage A: 5-nitro 2-phenyl anisole 50 ml of a 2M aqueous solution of sodium carbonate is added to a solution containing 12 g of 2-bromo 5-nitro anisole, 8.2 g of phenylboronic acid and 1.2 g of tetra (triphenylphosphine) palladium. The whole is heated under reflux for 7 hours, under vigorous agitation. The reaction medium is left to return to 20° C., it is poured into water and extraction is carried out with ethyl acetate. The organic phases are collected, dried and evaporated under reduced pressure. The product obtained is chromatographed on silica, eluting with a heptane-isopropyl ether mixture (9-1) and in this way 11.4 g of sought product is obtained, melting at 71° C.

Stage B: 3-methoxy4-phenyl aniline 2.6 g of 10% by weight of palladium on charcoal is added to a solution of 11.2 g of the product obtained in Stage A in 150 ml of ethyl acetate. The suspension obtained is agitated under 1.3 atmospheres of hydrogen. After the absorption of hydrogen has stopped, the reaction medium is returned to normal atmospheric pressure, followed by filtration and evaporation under reduced pressure in order to obtain 9.64 g of sought product melting at 56° C.

Stage C: 5-iodo 2-phenyl anisole 8 g of the product obtained in Stage B is dissolved at 40° C. in 60 ml of glacial acetic acid. Then a solution of 5 ml of concentrated sulphuric acid in 80 ml of water is added. The reaction medium is cooled down to 0° C. Then a solution of 2.77 g of sodium nitrite in 35 ml of water is added dropwise over one hour. Agitation is carried out for one hour at 0° C., and a solution of 13.33 g of potassium iodide, in 25 ml of water is added dropwise. The suspension obtained is maintained at 0° C. for one hour, brought to 10° C. over 40 minutes, maintained at 10° C. for one hour, and brought to 20° C. over 30 minutes. It is poured into water, and extraction is carried out with ethyl acetate. The organic phases are collected and washed (aqueous solution of NaHSO$_3$ then NaHCO$_3$). They are dried and evaporated under reduced pressure. The product obtained is chromatographed, eluting with a heptane-methylene chloride mixture (9-1) and 9.6 g of sought product is obtained, melting at 57° C.

Stage D: (5-iodo 2-phenyl) phenol 1.83 ml of boron tribromide is added dropwise at 0° C. under a nitrogen atmosphere to a solution containing 6 g of 4-iodo 2-methoxy biphenyl. Agitation is carried out for one hour at 0° C. then for 5 hours at 20° C. and the reaction medium is poured into a water and ice mixture. The suspension obtained is agitated for 15 minutes and extraction is carried out with methylene chloride. The organic phases are collected, dried and evaporated under reduced pressure. In this way 5.65 g of 4-iodo 2-hydroxy biphenyl is obtained.
Stage E: methyl (5-iodo 2-phenyl phenoxy) acetate 5.3 g of potassium carbonate is added to a solution containing 5.69 g of 4-iodo 2-hydroxy biphenyl and 1.82 ml of methyl bromoacetate. The suspension obtained is heated under reflux and under a nitrogen atmosphere for 2 hours 30 minutes, poured into water and extraction is carried out with methylene chloride. The organic phases are collected, washed, dried and evaporated under reduced pressure. The product obtained is chromatographed, eluting with a heptane-methylene chloride mixture (1-1) and 6.98 g of sought product is obtained, melting at 55° C.
Stage F: methyl(Z)2-[4-iodo (1,1'-biphenyl)2-yloxy]3-methoxy propenoate By operating as in the last stage of the preparations of Examples 1 and 2, the sought product was obtained, melting at 132° C.

EXAMPLE 10 methyl(Z)2-[2,4-dichloro5-[2-(trimethylsilyl)1-ethynyl]phenoxy]3-methoxy propenoate By operating as in Example 1 starting with the starting product described hereafter, the sought product was obtained, melting at 142° C.

NMR $CDCl_3$ ppm 0.28 (s) $Si(CH_3)_3$; 3.72 (s) and 3.89 (s) the $OCH_3$'s; 6.89 (s) $H_6$; 7.35 (s) ΔZ H; 7.41 (s) $H_3$.

Starting product of Example 10 methyl(Z)2-(5-bromo2,4-dichloro phenoxy)3-methoxy propenoate

The starting product of Example 10 was prepared as follows:
Stage A: 5-bromo 2,4-dichloro anisole 1 g of 5-bromo 2-chloro anisole and 0.66 g of N-chloro succinimide in 10 ml of acetic acid is heated at 90° C. for 20 hours. The reaction medium is poured into water, extraction is carried out with methylene chloride. The organic phase is washed with a saturated aqueous solution of sodium bicarbonate, dried over magnesium sulphate and evaporated under reduced pressure. 1.15 g of sought product is obtained.
Stage B: 5-bromo 2,4-dichloro phenol By operating as in Stage A of the preparation of the starting product of Example 1 and 2, the sought product was obtained.
Stage C: methyl (5-bromo 2,4-dichloro phenoxy) acetate The product was obtained from 5-bromo 2,4-dichloro phenol by operating as in Stage B of the starting product of Examples 1 and 2.
Stage D: methyl(Z)2-(5-bromo 2,4-dichloro phenoxy)3-methoxy propenoate By operating as in the last stage of the preparations of Examples 1 and 2, the sought product was obtained, melting at 153° C.

EXAMPLES 11 TO 16

By operating as indicated in the preceding examples, starting with the appropriate products obtained in a similar manner to that indicated in the above preparations of starting products, the following were obtained:

EXAMPLE 11 methyl(Z)3-methoxy2-[2-ethyl5-[2-(triethylsilyl)1-ethynyl]phenoxy]propenoate

M.p.=75° C.

EXAMPLE 12 methyl(Z)2-[2-bromo5-[2-(triethylsilyl)1-ethynyl]phenoxy]3-methoxy propenoate

M.p.=142° C.

EXAMPLE 13 methyl(Z)2-[2-chloro5-[2-(terbutyl dimethylsilyl)1-ethynyl]phenoxy]3-methoxy propenoate M.p.=137° C.

EXAMPLE 14 methyl(Z)2-[2-bromo methyl5-[2-(terbutyl dimethyl silyl)1-ethynyl]phenoxy 3-methoxy propenoate M.p.=105° C.

EXAMPLE 15 methyl(Z)2-[2-fluoro5-[2-(trimethylsilyl)1-ethynyl]phenoxy]3-methoxy propenoate

M.p.=132° C.

EXAMPLE 16 methyl(Z)2-[2-fluoro5-[2-(triethylsilyl)1-ethynyl]phenoxy]3-methoxy propenoate

M.p.=78° C.

EXAMPLE 17 methyl(Z)2-[2-fluoromethyl5-[2-(triethyl silyl)1-ethynyl]phenoxy]3-methoxy propenoate M.p.=86° C.

EXAMPLE 18 methyl(Z)2-[2-chloro5-[2-[dimethyl(n-octyl]1-ethynyl]phenoxy]3-methoxy propenoate M.p.=64° C.

EXAMPLE 19 methyl(Z)2-[2-chloro5-[2-[ethyl(dimethyl)silyl)1-ethynyl]phenoxy]3-methoxy propenoate M.p.=133° C.

EXAMPLE 20 methyl(Z)2-[2-chloro5-[2-(dimethyl)n-propyl)silyl)1-ethynyl]phenoxy3-methoxy propenoate M.p.=99° C.

EXAMPLE 21 methyl(Z)2-[2-chloro5-[2-[(n-butyl)(dimethyl)silyl]1-ethynyl]phenoxy]3-methoxy propenoate M.p.=49° C.

EXAMPLE 22 methyl(Z)2-[2-chloro5-[2-[(allyl)(dimethyl)silyl]1-ethynyl]phenoxy]3-methoxy propenoate M.p.=96° C.

EXAMPLE 23 methyl(Z)2-[2-chloro5-[2-[(2,2-dimethyl)(1,1,2-trimethyl)silyl]1-ethynyl]phenoxy]3-methoxy propenoate.

M.p.=83° C.

EXAMPLE 24 methyl(Z)2-[2-chloro5-[2-[trifluoropropyl)dimethyl) silyl]1-ethynyl]phenoxy]3-methoxy propenoate M.p.=100° C.

EXAMPLE 25 methyl(Z)2-[2-terbutyl5-[2-(triethylsilyl)1-ethynyl] phenoxy]3-methoxy propenoate Study of the Activity of the Compounds of the Invention Study of the Acaricide Activity on *Tetranychus Urticae*

Bean plants having 2 leaves infested with 30 females of *Tetranychus Urticae* per leaf are used which are put under an aerated hood under a constantly-illuminated ceiling. The plants are treated with a Fisher gun: 4 ml per plant of toxic solution of a mixture of equal volumes of water and acetone. The leaves are left to dry for half an hour then infestation is carried out. Mortality checks are carried out after 3 days.

Results

Starting from a dose of 100 ppm, the products of the invention show a significant acaricide activity.

Activity on *Plasmopara viticola*

6 weeks after sowing, vine plants of Riesling Ehrenfelder variety are soaked with an aqueous suspension of active ingredient.

Once the sprayed product is dry, the plants are inoculated with a suspension of *Plasmopara viticola* zoosporangia and the wet plants are placed in a chamber at 23° C. and with a relative atmospheric humidity of 80–90%.

After incubation for 7 days, the plants are placed in a culture chamber to encourage the development of the fungi. The extent of the infestation is then evaluated.

The degree of effectiveness of the products is evaluated relative to an infested untreated control.

At a concentration of less than 25 ppm, the products of Examples 1, 4 and 5 have an effectiveness close to 100%.

Activity on *Pyrenophora teres*

Barley plants of Igri variety at the "2-leaf" stage are soaked with an aqueous suspension of active ingredient.

Once the sprayed product is dry, the plants are inoculated with an aqueous suspension of *Pyrenophora teres* spores and left to incubate for 16 hours in a chamber with a relative atmospheric humidity of 100%. The infested plants are then left to develop in a greenhouse at 25° C. under a relative humidity of 80%.

A week after the inoculation, the extent of the disease is evaluated. The degree of effectiveness of the products is evaluated relative to an infested untreated control.

At a concentration of less than 25 ppm of active ingredient, the products of Examples 1, 4 and 5 have an effectiveness close to 100%.

Activity on *Erysiphe graminis*

"2-leaf" stage barley plants are inoculated with barley powdery mildew conidia (*Erysiphe graminés* p sp. *hordie*) and put in a greenhouse at 20° C. under a relative humidity of 50%, one day after the inoculation. The plants are then treated with an aqueous suspension of active ingredient. The signs of powdery mildew are sought. The degree of effectiveness is evaluated relative to an infested untreated control.

At a concentration of less than 25 ppm, the compounds of Examples 1, 4 and 5 have an effectiveness close to 100%.

Activity on *Leptosphaeria nodorum*

"2-leaf" stage wheat of Jubilar variety is soaked with an aqueous suspension of active ingredient. Once the sprayed product is dry, the plants are inoculated with an aqueous suspension of *Leptosphaeria nodorum* picnospores, and left to incubate for several hours in a chamber with a controlled environment, with a relative atmospheric humidity of 100%. The plants are left to develop in a greenhouse under a relative atmospheric humidity of 90% until symptoms of disease appear.

The degree of effectiveness is expressed relative to an infested untreated control.

At a concentration of less than 25 ppm, the compounds of the examples have an effectiveness of 100%.

What is claimed:

1. The compounds of formula (I):

$$
\text{R}_2-\underset{\underset{R_3}{|}}{\overset{\overset{R_1}{|}}{Si}}-C\equiv C-\underset{}{\text{(aryl)}}-O-\underset{H_3C-O}{\overset{}{C}}=\underset{}{\overset{}{C}}-CO_2CH_3
$$
(I)

in which:

R$_1$, R$_2$ and R$_3$, identical or different, represent a linear, branched or cyclic alkyl radical, an alkenyl or alkynyl radical, containing up to 8 carbon atoms, optionally substituted by one or more halogen atoms; an aryl radical optionally substituted by one or more halogen atoms, one or more hydroxyl radicals, one or more linear or branched alkyl radicals which may be, substituted by one or more halogen atoms; one or more O-alkyl or S-alkyl radicals optionally substituted by one or more halogen atoms;

X represents a hydrogen atom; a halogen atom; an alkyl, alkenyl, alkynyl, O-alkyl, O-alkenyl, O-alkynyl, S-alkyl, S-alkenyl or S-alkynyl radical, optionally substituted by one or more halogen atoms and containing up to 11 carbon atoms; an aryl radical containing up to 14 carbon atoms; a C≡N; NO$_2$; NH$_2$;

$$
\text{N}\begin{matrix}\text{alk}_1\\ \text{alk}_2\end{matrix};
$$

COO alk$_3$, wherein alk$_1$, alk$_2$, and alk$_3$ are identical to or different from each other and represent an alkyl radical containing up to 8 carbon atoms;

R$_4$ represents one of the values indicated above for X with the exception of hydrogen.

2. The compounds of formula (I) as defined in claim 1, in which the geometry of exo double bond is Z.

3. The compounds of formula (I) as defined in claim 1, in which R$_1$, R$_2$ and R$_3$ each represent an alkyl radical containing up to 4 carbon atoms.

4. The compounds of formula (I) as defined in claim 3 in which R$_1$, R$_2$ and R$_3$ each represent a methyl or ethyl radical.

5. The compounds of formula (I) as defined in claim 1, in which $R_4$ represents a halogen atom.

6. The compounds of formula (I) as defined in claim 1 in which $R_4$ represents an alkyl radical containing up to 4 carbon atoms.

7. The compounds of formula (I) as defined in claim 1 the names of which follow:

- methyl(Z)2-[2-chloro5-[2-(trimethylsilyl)1-ethynyl]phenoxy]3-methoxy propenoate,
- methyl(Z)3-methoxy2-[2-methyl5-[2-(trimethylsilyl)1-ethynyl]phenoxy]propenoate; and
- methyl(Z)3-methoxy2-[2-methyl5-[2-(triethylsilyl)1-ethynyl]phenoxy]propenoate.

8. Pesticide compositions containing as active ingredient at least one compound of formula (I) as defined in claim 1.

9. Insecticide compositions containing as active ingredient at least one compound of formula (I) as defined in claim 1.

10. Acaricide compositions containing as active ingredient at least one compound of formula (I) as defined in claim 1.

11. Fungicide compositions containing as active ingredient at least one compound of formula (I) as defined in claim 1.

* * * * *